United States Patent
Alison et al.

(10) Patent No.: US 6,790,838 B2
(45) Date of Patent: *Sep. 14, 2004

(54) COMBINATIONS AND METHODS FOR PROMOTING IN VIVO LIVER CELL PROLIFERATION AND ENHANCING IN VIVO LIVER-DIRECTED GENE TRANSDUCTION

(75) Inventors: Malcolm R. Alison, London (GB); Charles Coutelle, London (GB); Stuart J. Forbes, London (GB); Humphrey J. F. Hodgson, London (GB); Ildiko Sarosi, Newbury Park, CA (US); Michael Themis, Oxfordshire (GB)

(73) Assignees: Amgen, Inc., Thousand Oaks, CA (US); Imperial College Innovations LTD, London (GB)

(*) Notice: Subject to any disclaimer, the term of this patent is extended or adjusted under 35 U.S.C. 154(b) by 0 days.

This patent is subject to a terminal disclaimer.

(21) Appl. No.: 09/769,204

(22) Filed: Jan. 24, 2001

(65) Prior Publication Data

US 2002/0006902 A1 Jan. 17, 2002

Related U.S. Application Data

(63) Continuation of application No. 09/256,630, filed on Feb. 23, 1999, now Pat. No. 6,248,725.

(51) Int. Cl.[7] .................. A61K 48/00; A61K 15/63; C12N 38/43
(52) U.S. Cl. .................. 514/44; 424/93.1; 424/93.2; 424/198.1; 424/199.1; 435/456
(58) Field of Search .................. 514/44; 424/93.1, 424/93.2, 198.1, 199.1, 9.1, 9.2; 435/456

(56) References Cited

U.S. PATENT DOCUMENTS

| | | | |
|---|---|---|---|
| 5,650,504 A | 7/1997 | Bartley et al. | 536/23.5 |
| 5,712,163 A | 1/1998 | Parenteau et al. | 435/405 |
| 5,716,934 A | 2/1998 | Bartley et al. | 514/12 |
| 5,814,605 A | 9/1998 | Pierce et al. | 514/12 |
| 5,824,303 A | 10/1998 | Bartley et al. | 424/94.5 |
| 5,824,643 A | 10/1998 | Pierce et al. | 514/12 |
| 5,858,977 A | 1/1999 | Aukerman et al. | 514/12 |
| 5,900,404 A | 5/1999 | Gegg et al. | 514/12 |
| 6,248,725 B1 | 6/2001 | Alison et al. | 514/44 |

FOREIGN PATENT DOCUMENTS

| | | |
|---|---|---|
| WO | WO96/11949 | 4/1996 |
| WO | WO96/11951 | 4/1996 |
| WO | WO98/24813 | 6/1998 |

OTHER PUBLICATIONS

Scheur. P.J. Section 7.1: cirrhosis and chronic active hepatitis in Oxford Textbook of Clinical Hepatology, vol. 1, (McIntyre et al., eds.) Oxford University Press,1991.*
Rojkind et al. Section 7.2: Pathophysiology of liver fibrosis. in Oxford Textbook of Clinical Hepatology vol. 1, (McIntyre et al., eds.) Oxford University Press, 1991.*
Erlinger et al. Section 7.3: Cirrhosis: clinical aspects, in Oxford Textbook of Clinical Hepatology, vol. 1, (McIntyre et al., eds.) Oxford University Press, 1991.*
Verma et al.; Gene therapy– promises, problems and prospects, 1997,Nature , vol. 389:239–242.*
Marshall; Gene Therapy's growing Pains, 1995, Science ,vol. 269: 1050–1055.*
Orkins et.al.; Report and Recommendations of the Panel to Assess the NIH Investment in Research on Gene Therapy, 1995.*
Davern et. al.; Gene Therapy for Liver Disease, 1998, Digestive Diseases 16: 23–37.*
Ueki et.al.; Hepatocyte growth factor gene therapy of liver cirrhosis in rats, 1999, Nature Medicine, vol. 5: 226–230.*
Fujimoto; Hepatology: Microcirculation and Pathogenesis of Alcoholic Lives Injury, 2000, Journal of Gastroenterology and Hepatology 15: D33–D36.*
Alberts et al. Molecular Biology of the Cell, Second Edition, pp. 961–962.
Bosch et al. "Effects of keratinocyte and hepatocyte growth factor in vivo; implications for retrovirus–mediated gene transfer to liver", Hum Gene Ther, vol. 9, No. 12, (1998) pp. 1747–1754.
Cabrera et al. "Targeted retroviral gene transfer into the rat biliary tract", Somat Cell Mol Genet., vol. 22, No. 1, (1996) pp. 21–29.
Cai et al. "Therapeutic Levels of Human Protein C in Rats after Retroviral Vector–medicated Hepatic Gene Therapy," ©The American Society for Clinical Investigation, Inc., (Jun. 1998) vol. 101, No. 12, pp. 2831–2841.
Crystal, "Transfer of Genes to Humans: Early Lessons and Obstacles to Success." Science, vol. 270, pp. 404–410.
Deonarain, "Ligand–targeted receptor–mediated vectors for gene delivery." Exp. Opin. Ther. Patents, vol. 8, No. 1, pp. 53–69.
Forbes et al. Gestroenterology, vol. 118, (2000) pp. 591–598.
Gerolami et al. "Evaluation of HSV–tk Gene Therapy in a Rat Model of Chemically Induced Hepatocellular Carcinoma by Intratumoral and Intrahepatic Artery Routes," Cancer Research, vol 50, No. 4, (Feb. 15, 2000) and pp. 779–1152.
Grove et al., "Pre–clinical trials using hepatic gene delivery," Advanced Drug Delivery Reviews 30, (1998) pp. 199–204.

(List continued on next page.)

Primary Examiner—Anne-Marie Falk
Assistant Examiner—Daniel M. Sullivan
(74) Attorney, Agent, or Firm—Perkins Coie LLP

(57) ABSTRACT

Combinations and methods for inducing a semi-synchronous wave of liver cell proliferation in vivo and combinations and methods for inducing a semi-synchronous wave of liver cell proliferation and achieving transduction of proliferating liver cells in vivo are disclosed.

17 Claims, 3 Drawing Sheets

OTHER PUBLICATIONS

Kalodka et al., "Hepatic Gene Therapy: Efficient Retroviral–Mediated Gene Transfer into Rat Hepatocytes In Vivo," Somatic Cell and Molecular Genetics, vol. 19, No. 5, (1993) pp. 491–497.

Kolodka et al., "Gene therapy for diabetes mellitus in rats by hepatic expression of insulin," Proc. Natl. Acad. Sci. USA, vol. 92, (Apr. 1995), Medical Sciences, pp. 3293–3297.

Le et al., "Therapeutic Levels of Functional Human Factor X in Rats After Retroviral—Mediated Hepatic Gene Therapy," Blood, vol. 89, No. 4, (2/15) pp. 1254–1259.

Ledley et al., "Retroviral Gene transfer into primary hepatocytes: Implications for genetic therapy of liver–specific functions," Proc. Natl. Acad. Sci. USA, vol. 84 (Aug. 1987), Genetics, pp. 5335–5339.

Lucey et al., "Minimal criteria for placement of adults on the liver transplant waiting list: a report of a national conference organized by the American Society of Transplant Physicians and the American Association for the Study of Liver Diseases," Liver Transplantation and Surgery, vol. 3, pp. 628–637.

Miller et al., "Targeted vectors for gene therapy," Faseb J., vol. 9, pp. 190–199.

Murphy et al., American Cancer Society Textbook of Clinical Oncology, Second Edition. The American Cancer Society inc., Atlanta p. 290.

Pakkanen et al. "Enhanced plasma cholesterol lowering effect of retrovirus–mediated LDL receptor gene transfer to WHHL rabbit liver after improved surgical technique and stimulation of hepatocyte proliferation by combined partial liver resection and thymidine kinase–ganciclovir treatment," Gene Ther., vol. 6, No. 1, (1999) pp. 34–41.

Pakkanen et al. "Improved gene transfer efficiency in liver with vesicular stomatitis virus Ge–protein pseudotyped retrovirus after partial liver resection and thymidine kinase–ganciclovir pre–treatment," Pharmacol. Res., vol. 40, No. 5, (1999) pp. 451–457

Qi et al., "Blockade of type β transforming growth factor signaling prevents liver fibrosis and dysfunction in the rat," Proc. Natl. Acad. Sci. USA, vol. 96, (Mar. 1999), Medical Sciences, pp. 2345–2349.

Remington's Pharmaceutical Sciences, Mack Publishing Company: Easton, PA, 18th Edition, (1990) pp. 1303, 1304 and 1571.

Ruiz et al. "Gene therapy of viral hepatitis and hepatocellular carcinoma," J. Viral Hepatitis, vol. 6, (1999) pp. 17–34.

Themis et al. "Enhanced in vitro and in vivo gene delivery using cationic agent complexed retrovirus vectors," Gene Ther., (Sep. 1998) vol. 5, No. 9, pp. 1180–1186.

Andreadis. et al., Cell Cycle Dependence Of Retroviral Transduction: An Issue of overlapping time scales. Biotechnology and Bioengineering 58:272–281 (1998).

Angervo M. et al., Tri–iodothyronine and cycloheximide enhance insulin–like growth factor–binding protein–1 gene expression in human hepatoma cells, J. Mol. Endocrinol. 10(1):7–13 (1993).

Batshaw, Inborn errors of urea synthesis. Ann. Neurol. 35(2):133–141 (1994).

Bieniasz PD. et al., Cell cycle dependence of foamy retrovirus infection. J. Virol. 69(11):7295–9 (1995).

Bosch A. et al., Proliferation induced by keratinocyte growth factor enhances in vivo retroviral–mediated gene transfer to mouse hepatocytes. J. Clin. Invest. 98(12):2683–7 (1996).

Bowling WM, et al., Portal branch occlusion safely facilitates in vivo retroviral vector transduction of rat liver, Hum. Gene Ther. 7(17):2113–21 (1996).

Branchereau S. et al., Factors influencing retroviral–mediated gene transfer into hepatocytes in vivo. Hum. Gene Ther. 5(7):803–8 (1994).

Canzanelli, et al., Control of liver regeneration and nucleic acid content by the thyroid: with the observations on the effects of pyrimidines, Am.J.Physiol. 157:225–229 (1949).

Cardoso, et al., In situ retrovirus–mediated gene transfer into dog liver. Human Gene Therapy 4:411–418 at 412 (1993).

Chang and Wu, Gene therapy: applications to the treatment of gastrointestinal and liver diseases. Gastroenterology 106:1076–1084 (1994).

Choo Kll, et al., Molecular cloning of the gene for human anti–haemophilic factor IX, Nature. 299(5879):178–80 (1982).

Clarke DJ, et al., Genetic defects of the UDP–glucuronosyltranferase–1 (UGT1) gene that cause familial non–haemolytic unconjugated hyperbilirubinaemias, Clin. Chim. Acta 266(1):63–74 (1997).

Cosset FI., et al., High–titer packaging cells producing recombinant retroviruses resistant to human serum. J. Virol. 69(12):7430–6 (1995).

Demori I, et al., Tri–iodothyronine increases insulin–like growth factor binding protein–4 expression in rat hepatocytes. J. Endocrinol. 154(1):155–65 (1997).

Eisensmith & Woo, Somatic gene therapy for phenylketonuria and other hepatic deficiencies, J. Inher. Metab. Dis. 19:412–423 (1996).

Ferry N, et al., Retroviral–mediated gene transfer into hepatocytes in vivo. Proc. Nat'l Acad. Sci. USA. 88(19):8377–81 (1991).

Ferry & Heard, Liver–directed gene transfer vectors, Human Gene Ther. 9:1975–1981 (1998).

Fisher, et al., Recombinant adeno–associated virus for muscle directed gene therapy. Nat. Med. 3:306–312 (1997).

Forbes and Hodgson, Review article: gene therapy in gastroenterology and hepatology, Aliment. Pharmacol. Ther. 11:823–836 (1997).

Forbes SJ, et al., Retroviral gene transfer to the liver in vivo during tri–iodothyronine induced hyperplasia, Gene Ther. 5(4):552–5 (1998).

Francavilla A, et al., Hepatocyte proliferation and gene expression induced by triiodothyronine in vivo and in vitro, Hepatology 20(5):1237–41 (1994).

Horsthemke B. et al., Identification of a deletion in the low density lipoprotein (LDL) receptor gene in a patient with familial hypercholesterolaemia. Hum. Genet. 71(1):75–8 (1985).

Horwich, Inherited hepatic enzyme defects as candidates for liver–directed gene therapy. Curr. Top. Microbiol. Immunol 168:185–200 (1991).

Housley RM, et al., Keratinocyte growth factor induces proliferation of hepatocytes and epithelial cells throughout the rat gastrointestinal tract, J. Clin. Invest. 94(5):1764–77 (1994).

Hudig F, et al., Tri–iodothyronine prevents the amiodarone–induced decrease in the expression of the liver low–density lipoprotein receptor gene, J. Endocrinol. 152(3):413–21 (1997).

Ill, Charles R. et al., Optimization of the human factor VIII complementary DNA expression plasmid for gene therapy of hemophilia A, Blood Coagulation and Fibrinolysis. vol. 8. Suppl. 2. 1997.

Kay, et al., Hepatic gene therapy: persistent expression of human alpha l–antitrypsin in mice after direct gene delivery in vivo. Human Gene Therapy 3:641–647 at 642 (1992).

Kitraki E. et al., Hormonal control of insulin–like growth factor–II gene expression in the rat liver. J. Mol. Endocrinol. 9(2):131–6 (1992).

Knaan–Shanzer S. et al., Cell cycle state, response to hemopoietic growth factors and retroviral vector–mediated transduction of human hemopoietic stem cells. Gene Ther. 3(4):323–33 (1996).

Kosai KI, et al., Retrovirus–mediated in vivo gene transfer in the replicating liver using recombinant hepatocyte growth factor without liver injury or partial hepatectomy. Hum. Gene Ther. 9(9):1293–301 (1998).

Li, et al., In vivo gene therapy for hyperlipidemia: phenotypic correction in Watanabe rabbits by hepatic delivery of the rabbit LDL receptor gene. J. Clin. Invest. 93:768–773 (1995).

Lieber A. et al., Adenovirus–mediated urokinase gene transfer induces liver regeneration and allows for efficient retrovirus transduction of hepatocytes in vivo. Proc. Nat'l Acad. Sci. USA. 92(13).6210–4 (1995).

Lieber A. et al., A modified urokinase plasminogen activator induces liver regeneration without bleeding. Hum. Gene Ther. 6(8):1029–37 (1995).

Mann, et al., Construction of a retrovirus packaging mutant and its use to produce helper–free defective retrovirus. Cell 33:153–159 (1983).

Oinonen T, et al., Hormonal regulation of the zonated expression of cytochrome P–450 3A in rat liver, Biochem. J. 309 ( Pt 1):55–61 (1995).

Ott, et al., Simultaneous up–regulation of viral receptor expression and DNA synthesis is required for increasing efficiency of retroviral hepatic gene transfer. J. Biol. Chem. 273(19):11954–61 (1998).

Reich–Slotky R, et al., Chimeric molecules between keratinocyte growth factor and basic fibroblast growth factor define domains that confer receptor binding specificities, J. Biol. Chem. 270(50):29813–8 (1995).

Rettinger SD, et al., In vivo hepatocye transduction with retrovirus during in–flow occlusion. J. Surg. Res. 54(5):418–25 (1993).

Roe, et al., Integration of murine leukemia virus DNA depends on mitosis, EMBO J. 12:2099–2108 (1993).

Rusch, Sharyn L., et al., Protein transport via amino–terminal targeting sequences: common themes in diverse systems (Review). Molecular Membrane Biology 12, 295–307 (1995).

Sandig and Strauss, Liver–directed gene transfer and application to therapy. J. Mol. Med. 74:205–212 (1996).

Shima N. et al., Hepatocyte growth factor and its variant with a deletion of five amino acids are distinguishable in their biological activity and tertiary structure. Biochem. Biophys. Res. Commun. 200(2):808–15 (1994).

Stolz DB. et al., Comparative effects of hepatocyte growth factor and epidermal growth factor on motility, morphology, mitogenesis, and signal transduction of primary rat hepatocytes, J. Cell. Biochem. 55(4):445–64 (1994).

Strain AJ. et al., Native and recombinant human hepatocyte growth factors are highly potent promoters of DNA synthesis in both human and rat hepatocytes. J. Clin. Invest. 87(5):1853–7 (1991).

Von Heijne, Gunnar, Signal Sequences, The Limits of Variation, J. Mol. Biol. (1985) 184, 99–105.

Zarnegar R. et al., Expression of hepatocyte growth factor mRNA in regenerating rat liver after partial hepatectomy. Biochem. Biophys. Res. Commun. 177(1):559–65 (1991).

Zhang, W.–W., Antisense oncogene and tumor suppressor gene therapy of cancer. J. Mol. Med. 74:191–204 (1996).

Alberts. et al., Molecular Biology Of The Cell, 2d Edition, pp. 961–2.

Bosch, et al., Effects of keratinocyte and hepatocyte growth factor in vivo: implications for retrovirus–mediated gene transfer to liver. Hum Gene Ther 9(12):1747–54 (1998).

Cabrera. et al., Targeted retroviral gene transfer into the rat biliary tract. Somat Cell Mol Genet. 22(1):21–9 (1996).

Cai et al.: "Therapeutic Levels of Human Protein C in Rats after Retroviral Vector–medicated Hepatic Gene Therapy": ©The American Society for Clinical Investigation, Inc., vol. 101. No. 12. Jun. 1998. pp. 2831–2841.

Crystal, R.G. Transfer of Genes to Humans: Early Lessons and Obstacles to Sucess. Science 270:404–410.

Deonarain, M.P. Ligand–targeted receptor–mediated vectors for gene delivery. Exp. Opin. Ther. Patents 8(1):53–69.

Forbes S J et al.; "Tri–iodothyronine and dHGF synergistically enhance hepatocyte DNA synthesis in vivo and enable peripheral venous strategies for retroviral gene transfer." HEPATOLOGY, vol. 28, No. 4 Part 2, Oct. 1998, p. 503A XP000946022; Biennial Scientific Meeting of the International Association for the Study of the Liver and the 49th Annual Meeting and Postgraduate Courses of the American Association for the Study of Liver Diseases: Chicago, Illinois, USA: Nov. 4–10, 1998: ISSN:0270–9139 abstract.

Forbes SJ et al.: "Retroviral gene transfer to the liver in vivo without prior partial hepatectomy." Clinical Science (London), vol. 94, No. 2, Feb. 1998, p. 2P XP000946045; Meeting of the Medical Research Society; London, England, UK; Nov. 13–14, 1997; ISSN: 0143–5221 abstract.

Forbes et al., Gastroenterology, vol. 118, pp. 591–598.

Gerolami et al.; Evaluation of HSV–tk Gene Therapy in a Rat Model of Chemically Induced Hepatocellular Carcinoma by Intratumoral and Intrahepatic Artery Routes; Cancer Research Feb. 15, 2000, vol. 60, No. 4, pp. 779–1152.

Grove et al., "Pre–clinical trials using hepatic gene delivery", Advanced Drug Delivery Reviews 30 (1998) pp. 199–204.

Kolodka et al; "Gene therapy for diabetes mellitus in rats by hepatic expression of insulin"; Proc. Natl. Acad. Sci. USA, vol. 92, Apr. 1995. Medical Sciences. pp. 3293–3297.

Kolodka et al.; "Hepatic Gene Therapy: Efficient Retroviral–Mediated Gene Transfer into Rat Hepatocytes In Vivo": Somatic Cell and Molecular Genetics, vol. 19, No. 5, 1993, pp. 491–497.

Le et al., "Therapeutic Levels of Functional Human Factor X in Rats After Retroviral–Mediated Hepatic Gene Therapy"; Blood, vol. 89, No. 4 (Feb. 15). pp. 1254–1259.

Ledley et al.: "Retroviral gene transfer into primary hepatocytes: Implications for genetic therapy of liver–specific functions": Proc. Natl. Acad. Sci. USA, vol. 84, Aug. 1987. Genetics, pp. 5335–5339.

Lucey et al., "Minimal criteria for placement of adults on the liver transplant waiting list: a report of a national conference organized by the American Society of Transplant Physicians and the American Association for the Study of Liver Diseases": Liver Transplantation and Surgery. vol. 3, 628–637.

Miller et al. Targeted vectors for gene therapy. FASEB J. 9:190–199.

Murphy, G.P. et al. American Cancer Society Textbook of Clinical Oncology, Second Edition. The American Cancer Society Inc., Alanta.

Orkin, S.H. et al. Report and Recommendation of the Panel to Assess the NHI Investment in Research on Gene Therapy. National Institute of Health. Bethesda, Maryland.

Pakkanen, et al., Improved gene transfer efficiency in liver with vesicular stomatitis virus G–Protein pseudotyped retrovirus after partial liver resection and thymidine kinase–ganciclovir pre–treatment, Pharmacol Res. 40(5):451–7 (1999).

Pakkanen, et al., Enhanced plasma cholesterol lowering effect of retrovirus–mediated LDL receptor gene transfer to WHHL rabbit liver after improved surgical technique and stimulation of hepatocyte proliferation by combined partial liver resection and thymidine kinase—ganciclovir treatment. Gene Ther. 6(1):34–41 (1999).

Qi et al.; "Blockade of type β transforming growth factor signaling prevents liver fibrosis and dysfunction in the rat": Proc. Natl. Acad. Sci. USA, vol. 96. Mar. 1999. Medical Sciences. pp. 2345–2349.

Remington's Pharmaceutical Services, Mack Publishing Company: Easton, PA. 18th Edition. pp. 1303, 1304 and 1571.

Ruiz et al.; "Gene therapy of viral hepatitis and hepatocellular carcinoma"; Journal of Viral Hepatitis, 1999, 6, pp. 17–34.

Themis M. et al. Enhanced in vitro and in vivo gene delivery using cationic agent completed retrovirus vectors, Gene Ther. Sep. 1998; 5(9):1180–6.

* cited by examiner

COMBINATIONS AND METHODS FOR PROMOTING IN VIVO LIVER CELL PROLIFERATION AND ENHANCING IN VIVO LIVER-DIRECTED GENE TRANSDUCTION

This application is a Continuation of Ser. No. 09/256,630, filed on Feb. 23, 1999, now U.S. Pat. No. 6,248,725.

FIELD OF THE INVENTION

This invention relates to combinations and methods for inducing a semi-synchronous wave of liver cell proliferation in vivo and for combinations and methods for inducing a semi-synchronous wave of liver cell proliferation and transduction of proliferating liver cells in vivo.

BACKGROUND

Several characteristics make the liver an attractive target organ for the application of gene therapy. First, the liver is the situs of essential metabolic pathways, and consequently it is often the organ involved in genetic metabolic diseases. Data from model animals suggested that expression of a functional version of a gene in the liver of the affected animal can substantially restore metabolic function. Recent results obtained in human clinical trials have supported this view. The liver is also intimately associated with the circulatory system, and can serve as a secretory organ for the systemic delivery of therapeutic proteins or polypeptides. Another advantage the liver presents as an organ for gene therapy is the particular structure of its endothelium, which permits access of large molecules to the liver parenchyma. Vectors commonly used in gene therapy therefore can penetrate the organ and reach the liver cells.

Liver gene therapy has broad applicability, and can be used in the treatment and prevention of conditions by expression of RNAs, polypeptides or proteins, or combinations thereof, in the liver for action in the liver or secretion of polypeptides or proteins into the bloodstream or the gastrointestinal tract. Conditions that may be treated or prevented by liver gene therapy include, for example, inborn errors of metabolism, lymph and blood protein and polypeptide deficiencies, including for example, clotting abnormalities, obesity, hypercholesterolemia, cystic fibrosis, alpha 1-antitrypsin deficiency, phenylketonuria, diabetes, Wilson disease, ornithine transcarbamylase deficiency, among others, cancer, several forms of hepatitis and other infectious diseases affecting liver, hypertension, cirrhosis of the liver, among others.

Preventive and therapeutic applications of gene transfer to the liver have been recently reviewed in the literature. See, e.g., Davem, et al., Dig. Dis. 16:23–37 (1998); Forbes and Hodgson, Aliment. Pharmacol. Ther. 11:823–836 (1997); Chang and Wu, Gastroenterology 106:1076–1084 (1994); and Horwich, Curr. Top. Microbiol. Immunol. 168:185–200 (1991).

Some liver-directed gene therapy applications require long-term moderate to high level expression of a product encoded by a gene construct. To that end, it has been found desirable that the vector transduce a large proportion of target cells, and that the gene construct stably integrate into the genome of the transduced target cells. Transduction of gene constructs into the genome of liver cells has been accomplished by several means, including the use of retroviral vectors, adeno-associated virus vectors, lipofectant agents, receptor based-transfer, and combinations thereof. See, e.g., Sandig and Strauss, J. Mol. Med. 74:205–212 (1996). Cell division, in particular passage of a cell through the S phase of the cell cycle, has been found to greatly increase, and in some cases has been found indispensable, for integration of a transduced gene construct into a cell's genome or for its adequate expression. See, e.g., Roe, et al., EMBO J. 12:2099–2108 (1993)(retroviruses) and Fisher, et al., Nat. Med. 3:306–312 (1997)(adeno-associated virus). The induction of liver cells to proliferate has also been found to present other advantages for liver-directed gene transfer, including the up-regulation of viral receptor expression by dividing liver cells, which has a positive effect on the efficiency of retroviral vector gene transfer into liver cells. Ott, et al., J. Biol. Chem. 273(19):11954–61 (1998).

Retroviral vectors provide several advantages for in vivo gene transfer, including their ability to carry relatively large amounts of genetic material (8 kilobases (kb)) and their reliable, efficient and consistent integration into a target cell's genome. The use of recombinant retroviruses as gene transfer vectors into liver cells has nevertheless been limited due to methodological difficulties. The well documented quiescent state of liver cells under normal conditions has prevented efficient in vivo liver cell transduction by retroviral vectors because retroviral vectors require division of target cells within a few hours of vector entry for stable integration of the gene construct into the genome of the target cell.

While techniques have been described for inducing the proliferation and transduction of liver cells in vivo in model animals, these techniques have been found inadequate for general use. One presently used strategy, for example, depends on liver regeneration induced by removal of a large portion of the liver (Ferry, et al., Proc. Nat'l Acad. Sci. USA 88:8377–8381 (1991)), by causing apoptosis (cell death) of a large portion of the liver by portal branch occlusion (Bowling, et al., Human Gene Therapy 7:2113–2121 (1996)), or by producing severe liver damage by expression of toxic genes in liver cells (Lieber, et al., Human Gene Therapy 6:1029–37 (1995)). These techniques are laborious, intrusive and may result in complications due to the rapid elimination of a large portion of the liver of an individual. The need for major surgery before integrative transfer is clinically undesirable. Moreover, these techniques are particularly unsuitable for individuals in need of gene therapy due to an already present liver insufficiency.

Less invasive procedures for inducing replication of liver cells have been described, but these procedures have failed to solve the existing problem of low transduction, as they have been found to induce a low number of liver cells to proliferate, and generate an inadequately low proportion of transduced cells. For example, Bosch, et al., (J. Clin. Invest. 98:2683–2687 (1996)) reported that administration of keratinocyte growth factor will induce the proliferation of liver cells. However, only 2% of the hepatocytes in the liver were transduced when a retroviral vector was administered 24 hours after KGF administration.

Kosai, et al., (Human Gene Therapy 9:1293–1301 (1998)) reported that hepatocyte growth factor administration followed by retroviral vector administration will increase transduction of liver cells in vivo. However, low transduction values of 1.3% were achieved. Similarly, Forbes, et al., (Gene Therapy 5:552–555 (1998)) reported that triiodothyronine administration induced proliferation of liver cells in vivo, and when followed by retroviral administration increased transduction of liver cells in vivo. Again, however, low transduction values of about 1.3% were achieved.

Therefore, it is desired to provide less invasive and more efficient, effective and convenient compositions and methods for inducing a semi-synchronous wave of liver cell proliferation and for the transduction of an adequate quantity of liver cells without the need for hepatectomy of a large portion of the liver, or otherwise eliminating a large number of liver cells by either expressing a toxic gene in the liver or by causing the apoptotic death of a large number of liver cells by partial portal occlusion.

SUMMARY OF THE INVENTION

In a first, independent aspect of the present invention, a combination for inducing a semi-synchronous wave of liver cell proliferation in vivo includes KGF and T3.

In a second, independent aspect of the present invention, concurrent administration of an effective amount of T3 and KGF will synergistically induce a semi-synchronous wave of liver cell proliferation in vivo.

In a third, independent aspect of the present invention, in vivo induction of a semi-synchronous wave of liver cell proliferation using a combination including T3 and KGF prior to administration of a liver-directed gene transfer vector enhances transduction of liver cells in vivo.

In a fourth, independent aspect of the present invention, the concurrent administration of an effective amount of T3 and KGF, and the administration of a liver-directed gene transfer vector having an appropriate gene construct, is effective to express specific RNAs, proteins or polypeptides in the liver, or for the systemic delivery of proteins or polypeptides that may be accomplished from their production and secretion from the liver into the circulatory system or the gastrointestinal tract.

In a fifth, independent aspect of the present invention, an organ including liver cells induced to proliferate by the concurrent administration of an effective amount of T3 and KGF and transduced by a liver-directed gene transfer vector is disclosed.

DETAILED DESCRIPTION OF THE INVENTION

Figure 1:
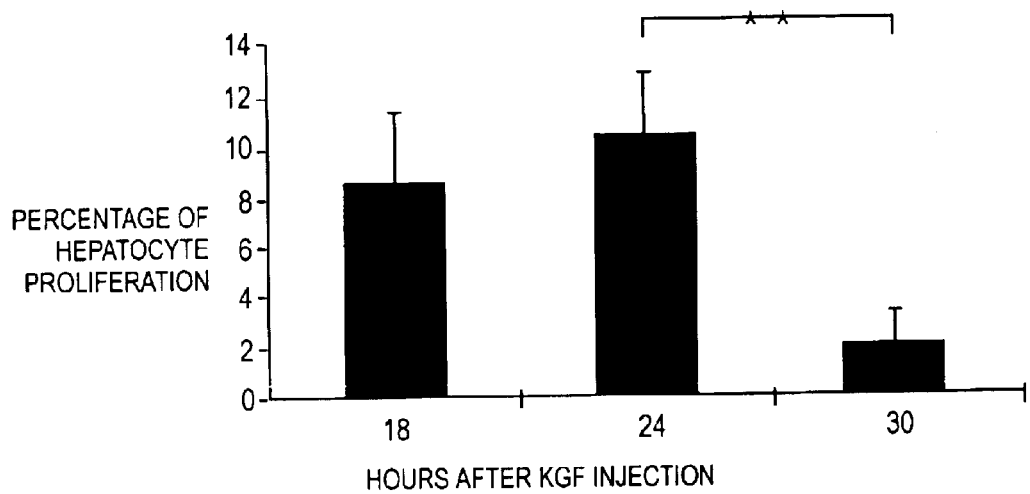
FIG. 1 is a bar graph representing the time course of hepatocyte proliferation in vivo following a single administration of KGF (1 mg/kg). Animals were sacrificed at 6 hour intervals, one hour prior to sacrifice all rats were injected with BrdU. Hepatic BrdU incorporation was detected in 4 μm sections by a monoclonal antibody, as described in detail in the examples infra. The proportion of BrdU labeled nuclei was quantified from 2000 hepatocytes per section. Results represent mean±S.D. "**" indicate a $p<0.05$.

As used herein, "organ" means a discrete group of cells related by function, as may be used, for example, for transplantation or in a life support system, or the like.

As used herein, time is measured from the first administration of a growth factor to the individual, and is considered "hour 0" of "day 1."

As used herein, "semi-synchronous" means that although the cells that are induced to proliferate do not enter S-phase at exactly the same time, they do so relatively contemporaneously, such that the first induced cell divisions and the last induced cell divisions occur within a period of between about 0 hours and about 28 days, depending on the species, weight, and other variables affecting induced liver cell proliferation and the quantity and the regimen of factor administration.

As used herein, "tri-iodothyronine" or "T3" refers to thyroid hormone or its analogs, and also includes compounds that bind and activate the thyroid hormone nuclear receptor.

The timing, dosage and ode of T3 administration should be determined by the prescribing physician or veterinarian, and may vary depending on the mode of administration, the species, age, and condition of the individual and in accordance with the needs of the individual and the time schedule of administration of other factors. T3 may be administered at any effective time before entrance of liver cells into S-phase is desired. T3 administration may also continue thereafter. Generally, however, T3 may be dministered between about 0 and about 28 days before entrance of liver cells into S-phase is desire. Preferably, T3 is administered between about 6 days and about 14 days before entrance of liver cell into S-phase is desired. Most preferably, T3 is administered between about 24 hours and about 8 days before entrance of liver cells into S-phase is desired. More than one administration of T3 may be desirable in accordance with the needs of the individual as determined by the prescribing physician or veterinarian, and T3 may be administered any effective amount of times. Successive ad inistrations generally can be performed at intervals ranging from about hourly to about weekly, but are preferably done at about daily intervals, or by continuous infusion. T3 administration may continue for any effective time after liver cells have begun to proliferate.

T3 may be administered in any effective daily dosage. In general, however, daily dosages will range from about 80 μg of T3 per kg of body weight per day (μg/kg) to about 80 mg/kg. Preferably, T3 is administered in daily dosages ranging from about 400 μg/kg to about 40 mg/kg. Most preferred is the administration of daily dosages of about 4 mg/kg of T3. T3 may be administered by any effective route. It may be administered, for example, intravenously ("IV"), intramuscularly ("IM"), intraperitoneally, directly into the liver, subcutaneously, orally, inhaled, or by suppository. Subcutaneous administration is preferred. For subcutaneous administration, T3 may be dissolved in an appropriate volume of 0.01 M NaOH in 0.9 M NaCl, or any other effective carrier, and administered as a bolus. The formulation of T3 for administration is well known in the art.

As used herein, "keratinocyte growth factor" or "KGF" refers to the keratinocyte growth factor polypeptide or one of its analogs, or alternatively an active fragment of keratinocyte growth factor or one of its analogs, or a factor that binds and activates the keratinocyte growth factor receptor. Preferred is the recombinantly produced form of KGF. See, e.g., U.S. Pat. No. 5,731,170, and PCT Application No. WO 90/08771, published Aug. 9, 1990 (directed to full length forms of KGF and variants); and PCT Application No. WO 96/11949, published Apr. 25, 1996; PCT Application No. WO 96/11951, published Apr. 25, 1996; and PCT Application No. WO 98/24813, published Jun. 11, 1998 (directed to stable analogs of KGF) all of which are incorporated herein by reference in their entirety, including figures.

The timing, dosage and mode of KGF administration should be determined by the prescribing physician or veterinarian, and may vary depending on the mode of administration, the species, age, and condition of the individual, and in accordance with the needs of the individual and the time schedule of administration of the other factors. KGF may administered at any effective time before entrance of liver cells into S-phase is desired. KGF administration may also continue thereafter. Generally, however, KGF may be administered between about 0 and about 28 days before entrance of liver cells into S-phase is desired. Preferably KGF is administered between about 6 hours and about 14 days before entrance of liver cells into S-phase is desired. Most preferably, KGF is administered as a single bolus between about 24 hours and about 8 days before entrance of liver cells into S-phase is desired. More than one administration of KGF may be desirable in accordance with the needs of the individual as determined by the prescribing physician or veterinarian, and KGF may be administered any effective amount of times. Successive administrations generally can be performed at intervals ranging from about hourly to about weekly, but are preferably done at about daily intervals, or by continuous infusion. KGF administration may continue for any effective time after liver cells have begun to proliferate, but preferably for not longer than about 12 days thereafter. KGF may be administered in any effective daily dosage. In general, however, daily dosages ranging from about 5 μg/kg to about 20 mg/kg. Preferably, KGF is administered in daily dosages ranging from about 100 μg/kg to about 10 mg/kg. Most preferred is the administration of daily dosages of about 1 mg/kg of KGF. KGF may be administered by any effective route. It may be administered, for example, IV, IM, intraperitoneally, directly into the liver, subcutaneously, orally, by suppository, or by production in situ in the liver after liver transduction with an effective vector with a gene construct for KGF expression, or the like, for example an adenovirus vector, or the like. Subcutaneous administration as a bolus is preferred. For subcutaneous administration, KGF may be dissolved in any effective buffer. For example lyophilized KGF may be reconstituted in a 0.01% by weight polyoxyethylenesorbitan monolaurate solution (Sigma) (TWEEN 20), or any other effective buffer. Other suitable buffers are well known in the art.

A triple combination of T3, KGF, and hepatocyte growth factor (HGF) was also tried. The cell proliferating characteristics and the transduction efficiency of the triple combination were not statistically significantly differen from the T3/KGF combination, although in some experiments the total number of cells induced to p oliferate and liver cells transduced may have been slightly higher.

In accordance with the present invention, the factors may be administered in any effective order or time interval. However, the factors are preferably "concurrently administered," meaning that independent of the order in which the factors are administered, the factors are administered within a time interval such that the effect of the factors on the proliferation of liver cells is at least greater than additive. The factors may also be administered together. Preferably, dividing liver cells in a quantity about 10% or greater than the sum of the quantity of cells that would have resulted had the factors been independently administered will result from concurrent administration. Most preferably, dividing liver cells in a quantity about 30% or greater than the sum of the quantity of liver cells that would have resulted had the factors been independently administered will result from the concurrent administration.

In accordance with the present invention, each factor may be independently administered any effective number of times, including more than once, as may be indicated by a physician or veterinarian.

In accordance with the present invention, the factors may be administered in any effective amount. However, preferably administration of an "effective amount" will be an amount of each factor such that when administered in combination with the other factor or factors the effect of the factors on the induction of in vivo liver cell proliferation is synergistic. In accordance with the present invention, the amount of each factor administered is such that the effect of the factors on the proliferation of liver cells is at least greater than additive. Preferably, proliferating liver cells in a quantity about 10% or greater than the sum of the quantity of liver cells that would have resulted had the factors been independently administered in those amounts will result from the concurrent administration of an effective amount of each factor. Most preferably, proliferating liver cells in a quantity about 30% or greater than the sum of the quantity of liver cells that would have resulted had the factors been independently administered in those amounts will result from the concurrent administration of an effective amount of each factor.

The utility of the administration of any particular amount of each factor and the time and regimen for the administration of the different factors will vary according to several variables, including the species, weight, and other variables, and must be evaluated empirically. It is within the skill of the art to modify the procedure and produce the desired effect in a specific subject.

Several liver-directed gene transfer vectors may be used in accordance with the present invention, including retroviral vectors, adeno-associated virus vectors, lipofectant agents, receptor based transfer, and combinations thereof. See Ferry & Heard, Human Gene Ther. 9:1975–1981 (1998). Preferred are retroviral vectors. The production and use of retroviral vectors as gene transfer vectors is well documented in the literature, including the articles by Mann, et al., Cell 33:153–159 (1983), Cosset, et al., J. Virol. 69(12): 7430–7436 (1995), which hereby incorporated by reference in their entirety. Production of retroviral vector as described by Cosset, et al., is preferred. Most preferred is the administration of a retrovirus complexed with cationic liposomes, in particular the cationic liposome DiOctadecylamidoGlycylSpermine (DOGS). Infectivity of retroviral vectors has been found to be increased by the addition of DOGS to the retroviral vector preparations.

In accordance with the present invention, a liver-directed vector is preferably administered such that it transduces the liver cells within a few hours of maximal liver-cell division. However, the vector may be administered prior to or after that time, as may be more effective, depending on the mode of administration of the vector, the species, age, condition, and in accordance with the needs of the individual as determined by the prescribing physician or veterinarian. Generally, however, the vector may be administered between about 0 and about 28 days after administration of the factors. Preferably the vector is administered between about 6 hours and about 14 days after factor administration. Most preferably, the vector is administered between about 24 hours and about 8 days after factor administration. More than one administration of vector may also be desirable in accordance with the needs of the individual as determined by the prescribing physician or veterinarian. These successive administrations generally can be performed at intervals ranging from hourly to weekly, but are preferably done at between about 6 and about 24 hour intervals.

The method of administering the liver-directed vector to the liver contemplated in accordance with the present invention will vary in accordance with the needs of the individual as determined by the physician or veterinarian. In general, however, in vivo liver transduction may be performed according to a modified method described in Rettinger, et al., J. Surg. Res. 54:418–425 (1993), which is hereby incorporated by reference in its entirety. The modified method of Rettinger is preferred. Subjects are anesthetized, and a laparotomy is performed. The portal vein and hepatic artery are clamped using micro-aneurysm clips, or the like, and the portal vein is cannulated with a needle having an appropriate gauge (according to the size of the subject) proximal to the clip and retroviral supernatant is injected. Hemostasis may be achieved by direct pressure to the portal vein and topical thrombin application, or the like. The clips are removed and the abdomen sutured, and the subjects are allowed to convalesce. See Forbes, et al., Gene Therapy 5:552–555 at 554 (1998), which is hereby incorporated by reference in its entirety.

Alternatively, the procedure may be accomplished with portal injection of the liver-directed vector, in which case the portal vein is cannulated and the vector solution pumped into the portal vein over a period of time. See, e.g., Kay, et al., Human Gene Therapy 3:641–647 at 642 (1992) (using 1 ml of viral supernatant in 8 $\mu$g/ml Polybrene infused over 50 minutes in mice), which is hereby incorporated by reference in its entirety.

Alternatively, the vector is delivered by asanguineous perfusion of the liver, whereby the liver is selectively perfused after excluding normal blood flow from the liver. This may be accomplished by clamping the hepatic artery, portal vein, suprahepatic vena cava, right suprarenal vein and infrahepatic vena cava to achieve the total vascular exclusion of the liver. The portal vein is then cannulated with a catheter of appropriate gauge, while an incision is made in the anterior wall of the infrahepatic vena cava, with a suction cannula placed into the vena cava to collect outflow. Liver perfusion, preferably single pass perfusion, is then performed using a pump. Flow rate may range from 0.1 ml/min per gram of liver to 10 ml/min per gram of liver. A rate of 1 ml/min per gram of liver is preferred, and may be increased to ensure satisfactory perfusion of the organ. After perfusion, the portal and caval vein incisions are sutured and the liver is revascularized. Cardoso, et al., Human Gene Therapy 4:411–418 at 412 (1993), which is hereby incorporated by reference in its entirety.

Alternatively, another preferred method of vector administration is by peripheral vein intravenous injection. The vector may be administered by intravenous injection any number of effective times, including more than once, as may be indicated by a physician or veterinarian. The intravenous injection may be administered at any effective time, as described supra, but is most preferably administered 18–36 hours after the administration of the growth factors.

Infectivity of liver directed vectors, in particular retroviral vectors, and hepatic transfection efficiency can be increased by the addition of liposomes, preferably cationic liposomes, to the liver directed vector preparations. The cationic liposome DiOctadecylamidoGlycylSpermine (DOGS) is preferred. DOGS is effective in concentrations of about 1 to about 30 $\mu$g per ml. Preferred is a final DOGS concentration of about 5 $\mu$g per ml. The titer of vector/DOGS solution administered has preferably about $1 \times 10^9$ i.u./ml after ultrafiltration.

Any effective volume of vector may be administered. The volume to be administered will depend on the i.u./ml of vector preparation, and the total number of i.u. it is desired to administer. In general, however, given a vector preparation having $1 \times 10^9$ i.u./ml, about 0.1 ml of vector preparation per kg of subject weight to about 80 ml of vector preparation per kg of subject weight may be administered. Most preferred is the administration of about 8 ml of a solution of $1 \times 10^9$ i.u./ml per kg of subject weight. Although any effective amount of total i.u. may be administered, preferably a total of about $8 \times 10^9$ i.u. per kg of subject weight are administered.

Examples of conditions which are effectively treated with the combinations and methods of the present invention include treatment and prevention of any conditions that may be prevented or ameliorated by the proliferation of liver cells, including liver cell deficiencies, cirrhosis of the liver, and the like. Other conditions which are effectively treated with the combinations and methods of the present invention include treatment and prevention of any conditions that may be prevented or ameliorated by the expression in the liver of RNAs, polypeptides or proteins, or combinations thereof, for action in the liver or secretion of polypeptides or proteins into the bloodstream or the gastrointestinal tract.

The liver directed vector includes a nucleic acid engineered such that it encodes the RNA, protein or polypeptide to be expressed, operably linked to a sequence, such as a promoter or the like, and alternatively also an enhancer or the like, such that the encoded RNA, or mRNA for the polypeptide or protein, will be transcribed in the liver cells. If a protein or polypeptide is to be expressed, the nucleic acid is preferably engineered such that when the mRNA is transcribed it has a sequence such that it may be translated. See, e.g., Ill, et al., Blood Coagulation and Fibrinolysis 8(Suppl 2):S23–S30 (1997)(incorporated herein by reference in its entirety).

The methods and compositions described herein find particular utility in the expression in the liver of RNAs, proteins and polypeptides known to have a therapeutic effect, including, but not limited to, for example, afamin (see, e.g., U.S. Pat. Nos. 5,652,352 and 5,767,243, hereby incorporated by reference including drawings); anti-inflammatory CD14 peptides (see, e.g., U.S. Pat. No. 5,766,593, hereby incorporated by reference including drawings); art (see, e.g., U.S. Pat. No. 5,766,877, hereby incorporated by reference including drawings); erythropoietins (see, e.g., U.S. Pat. Nos. 4,703,008, 5,441,868, 5,618,698, 5,547,933, 5,621,080 and 5,756,349, hereby incorporated by reference including drawings); granulocyte colony-stimulating factor (see, e.g., United States Patent Nos. hereby incorporated by reference including drawings); granulocyte-colony stimulating factors (see, e.g., U.S. Pat. Nos. 4,810,643, 4,999,291, 5,581,476, 5,582,823 (human) and 5,606,024 (canine) and PCT Publication Nos. 91/05795, 92/17505 and 95/17206, hereby incorporated by reference including drawings); interferon consensus (see, e.g., U.S. Pat. Nos. 5,661,009, 5,372,808, 5,541,293, 4,897,471, and 4,695,623, hereby incorporated by reference including drawings); interleukins (see, e.g., U.S. Pat. Nos. 5,075,222, hereby incorporated by reference including drawings); leptin (OB protein) (see, e.g., PCT Publication Nos. 96/40912, 96/05309, 97/00128, 97/01010 and 97/06816, hereby incorporated by reference including drawings); NDF peptides (see, e.g., U.S. Pat. No. 5,670,342, hereby incorporated by reference including drawings); platelet-derived growth factor B (see, e.g., U.S. Pat. Nos. 5,428,135, 5,272,064 and 5,149,792 hereby incorporated by reference including drawings); progenitor B cell stimulating factor (see, e.g., U.S. Pat. No. 5,580,754, incorporated herein be reference in its entirety); stem cell factor interleukin-6 (see, e.g., U.S. Pat. No. 5,610,056, hereby incorporated by reference including drawings).

The construct may include sequences encoding proteins engineered such that they will be secreted (see, e.g., U.S. Pat. No. 5,541,083, hereby incorporated by reference including drawings; von Heijne, J. Mol. Biol. 184:99–105 (1985) and references therein, incorporated herein by reference; Rusch & Kendall, Mol. Memb. Biol. 12:295–307 (1995) and references therein, incorporated herein by reference).

In addition, other RNAs, proteins and polypeptides that may be expressed include, but are not limited to insulin; gastrin; prolactin; adrenocorticotropic hormone (ACTH); luteinizing hormone (LH); follicle stimulating hormone (FSH); human chorionic gonadotropin (HCG); motilin; interferons (alpha, beta, gamma); tumor necrosis factor-binding protein (TNF-bp); interleukin-1 receptor antagonist (IL-Ira); brain derived neurotrophic factor (BDNF); glial derived neurotrophic factor (GDNF); neurotrophic factor 3 (NT3); fibroblast growth factors (FGF); neurotrophic growth factor (NGF); bone growth factors such as osteoprotegerin (OPG); insulin-like growth factors (IGFs); macrophage colony stimulating factor (M-CSF); granulocyte macrophage colony stimulating factor (GM-CSF); megakaryocyte derived growth factor (MGDF); keratinocyte growth factor (KGF); thrombopoietin; platelet-derived growth factor (PGDF); colony stimulating growth factors (CSFs); bone morphogenic protein (BMP); superoxide dismutase (SOD); tissue plasminogen activator (TPA); urokinase; streptokinase; kallikrein; interleukin genes; cystic fibrosis transmembrane conductance regulator; human factor VII; interleukin receptor antagonist proteins; cytokines; 4-hydroxyphenylpyruvic acid dioxygenase; tissue-type plasminogen activator or plasminogen; transferlphafetoprotein and albumin genes; glucuronosyltransferase; thrombopoietin; immunoregulatory cytokines; phenylalanine hydroxylase; ribozymes; dominant negative genes, and the like; cytochrome genes; immunoglobulin A (Busch, et al., Gastroenterology 115(1):129–38 (1998) incorporated herein by reference); canalicular bile salt transporters; bilirubin uridine diphosphate glucuronosyltransferase; multidrug resistance genes; organic anion transporters; bile salt transporters; ABC transporters, and the like, and other membrane proteins including transporters, receptors, cell adhesion molecules, and the like.

The term protein, as used herein, includes peptides, polypeptides, consensus molecules, analogs, derivatives or combinations thereof. Also included are those proteins with amino acid substitutions which are "conservative" in that they do not affect the intended function of the protein. See generally, Creighton, Proteins, W. H. Freeman and Company, N.Y., (1984) 498 pp. plus index, passim.

Other conditions that may be treated by the compositions and methods of the present invention include inborn errors of metabolism; lymph and blood protein and polypeptide deficiencies or overexpression; cancer (see, e.g., Zhang, W. -W., J. Mol. Med. 74:191–204 (1996)); the several forms of hepatitis and other infectious diseases affecting the liver; hypertension; clotting abnormalities including hemophilia A (Factor XIII deficiency), hemophilia B (Factor IX deficiency) and proteins C and S; obesity; hypercholesterolemia; cystic fibrosis; alpha 1-antitrypsin deficiency; cirrhosis of the liver; diabetes; ornithine transcarbamylase deficiency and other urea cycle related conditions (see Batshaw, Ann. Neurol. 35(2):133–141 (1994)); tryosinemia; phenylketonuria (see Eisensmith & Woo, J. Inher. Metab. Dis. 19:412–423 (1996)); haemochromatosis; carbohydrate disorders, including for example, the several glycogen storage diseases (including glucose-6-phosphatase deficiency); galactosemia and fructose intolerance; lysosomal storage deficiencies; CPS deficiency; FAH deficiency; propionic acidemia; methylmalonic acidemia; defects of branch amino acid degradation (maple syrupe urine disease); lipid metabolism, including LDL receptor deficiency (see Li, et al., J. Clin. Invest. 95:768–773 (1995)), and expression of apoA1 gene for increases in serum HDL levels; porphyrin metabolism by adding porphobilinogen deaninase activity; Wilson disease (copper-transporting ATPase); hyperbilirubemias, including Crigler-Najjar syndrome and Gilbert Syndrome (UDP-glucuronosyltransferase); Dubin-Johnson syndrome (cMOAT); expression of hammerhead ribozymes to cleave hepatitis C virus RNA and inhibit viral protein translation; expressing dominant negative genes, including for example mutants of the hepadnaviral core protein as antiviral agents; correction of Protein C deficiency; correction of Factor X deficiency; expression of antisense RNA, for example anti-sense RNA complementary to hepatitis B virus to inhibit viral proliferation, or to other protein to inhibit its expression; correction of citrullinaemia; expression of p53 to inhibit tumor progression; expression of leptin for obesity; expression of Alpha 1-antitrypsin to treat emphysema; expression of apolipoprotein B mRNA-editing complex to reduce LDL levels; inflammatory bowel disease by expressing immunoregulatory cytokines; attenuation of hypertension and cardiac hypertrophy and renal injury by expression of Kallikrein gene; treatment of tyrosinemia type 1; treatment of diabetes by expression of insulin gene, in particular under a glucose responsive promoter/enhancer; treatment of hyperlipidemias associated with apolipoprotein E and LDL receptor deficiencies by expression of human lipoprotein lipase; expression of phenylalamine hydroxylase for phenylketonuria; treatment of hypertriglyceridemia and impaired fat tolerance by expression of lipoprotein lipase; cancer gene therapy; correction of mitochondrial enzyme deficiencies; treatment of mucopolysaccharidosis type VII; secretion of cloned immunoglobulins, including antibodies; treatment of alpha-galactosidase A deficiency and Fabry disease; treatment of dwarfism by expression of growth hormone; treatment of tetrahydrobiopterin deficiency in hyperphenylalaninemic patients by gene transfer of 6-pyruvoyl-tetrahydropterin synthase; correction of diabetic alterations by glucokinase; treatment of type 1 hyperoxaluria; expression of the enzyme apobec-1 for hypercholesterolemia in LDL receptor-deficiency; treatment of familial hypercholesterolaemia by expression of the VLDL receptor gene; expression of human pyruvate kinase (PK) for gene therapy of human PK deficiency; correction of methylmalonyl-CoA mutase deficiency; treatment of phenylalanine hydroxylase deficiencies; adenosine deaminase and purine nucleoside phosphorylase deficiencies, and the like.

The methods and compositions of the present invention are also applicable for in vivo gene immunization, by direct expression of antigens in the liver, for example.

The present invention also finds applications in animal sciences and for veterinary uses. For example, the present invention is applicable in expressing RNA, proteins and polypeptides in the liver of animals—for action within the liver, or for secretion into the circulation or gastrointestinal tract. The long-term expression, inducible expression, or responsive expression of growth hormone, or growth hormone releasing substances like growth hormone releasing hormone, for example, in adult lactating cows may be achieved without causing the adverse consequences that the constitutive expression of the gene products may have in calves. Similarly, for example, the expression of leptins in farm animals an effective amount of time prior to slaughter for the production of leaner meat, without the adverse consequences such expression would have had had the leptins been expressed in growing and developing animals. The expression of major histocompatibility complex (MHC) molecules, and the like, in cells of the liver of an animal may be altered, for example, by expression of specific MHC molecules, or by inhibition of expression of MHC molecules by anti-sense RNA expression prior to organ transplantation. The methods and compositions may also be used in avian species, for example to produce avian growth hormones, or the like (see, e.g., U.S. Pat. Nos. 5,151,551 and 5,162,215, incorporated herein by reference in their entirety, including figures). The sequence of the RNAs, polypeptides or proteins encoded by the liver directed gene transfer vector is preferably conspecific.

The combination of factors of the present invention may also be used to enhance the proliferation and transduction of liver cells in vitro.

EXAMPLES

Unless otherwise specified, the following procedures were used throughout the following examples.

Male Wistar rats weighing 200–250 grams were used. They were housed in a temperature and light controlled room (12 hour light/dark cycle) and were allowed water and food ad libitum.

T3 (Sigma, St. Louis, Mo. USA), 4 mg per kilogram of body weight was dissolved in 100 µl of 0.01 M NaOH in 0.9 M NaCl and administered by subcutaneous injection in the flank region of the animal.

Lyophilized KGF (full lenght recombinant KGF, AMGEN, Thousand Oaks, Calif.) 1 mg per kilogram of body weight was dissolved in 100 µl of a suitable buffer (0.01% by weight polyoxyethylenesorbitan monolaurate (TWEEN 20, Sigma) solution) and administered by subcutaneous injection in the flank region of the animal.

Measurement of liver cell proliferation was performed by BrdU labeling. BrdU (Sigma) (50 mg/kg dissolved in 800 µl of 0.9% NaCl) was injected intraperitoneally 1 hour prior to sacrifice. Livers of the animals were removed and fixed in 60% methanol, 30% chloroform and 10% glacial acetic acid before routine histological processing and embedding in wax blocks. The incorporation of BrdU into hepatic nuclei was detected in 4 µm thick sections using a mouse monoclonal antibody (Dako, Glostrup, Denmark), followed by a biotinilated rabbit anti-mouse secondary antibody (Dako). Visualization was achieved by the indirect peroxidase technique using diaminobenzidine tetrahydrochloride dihydrate (Aldrich Chemical, Milwaukee, Wis. USA) as a substrate. The labeling index and percentage of hepatic mitoses was determined by counting 2000 hepatocytes per section from consecutive light microscopy fields. See Forbes, et al., Gene Therapy 5:552–555 at 553 (1998)(incorporated herein by reference in its entirety).

In vivo liver transduction was according to a modified method described in Rettinger, et al., J. Surg. Res. 54:418–425 (1993). Animals were anesthetized with isoflurane. A midline laparotomy was performed, the bowel was deflected to the left and wrapped in normal saline-soaked gauze. The portal vein and hepatic artery were clamped using micro-aneurysm clips, the portal vein was cannulated with a 26-gauge needle proximal to the clip and 1 ml of retroviral supernatant was injected over 5 minutes. Hemostasis was achieved by direct pressure to the portal vein and topical thrombin (Sigma) application. The clips were removed and the abdomen sutured, and the animals were allowed to recover in a warm, quite environment. See Forbes, et al., Gene Therapy 5:552–555 at 554 (1998). For peripheral vein injection, 1 ml of the retrovirus/DOGS complex was injected via tail vein as a bolus.

Transduction of liver cells was measured by β-galactosidase activity. Animals were anesthetized and sacrificed by exsanguination. The liver was removed and frozen in liquid nitrogen. Ten-micron frozen sections were cut on to glass slides, fixed in a solution of 1.25% glutaraldehyde at 4° C., washed with phosphate buffered saline (PBS) then covered in X-gal (Gibco BRL, Grand Island, N.Y.) solution (1 mg/ml, pH 7.4) and incubated overnight at 37° C. Sections were then washed in PBS, counterstained lightly with eosin or carmalum stain, dehydrated and mounted in pertex (Cellpath, Hemel Hempstead, UK). The proportion of hepatocytes expressing nuclear β-galactosidase was calculated by counting 2000 hepatocytes per section from three separate areas.

High titer amphotropic retroviral vector stocks were generated by the method described in Cosset, et al., J. Virol. 69:7430–7436 (1995). TELCeb/AF-7 cells were used to generate high titers of amphotropic retrovirus vector stock. This is a high titer replication defective vector encoding the gene for β-galactosidase together with a nuclear localization signal. Cells were grown in DMEM supplemented with 10% fetal calf serum at 37° C. To prepare viruses, cells were grown to confluency and refed with fresh medium overnight. The following day, virus containing supernatants were harvested and filtered though 0.4 µm filters for determination of retrovirus titer and helper virus assay. Retrovirus titer and helper virus assay were determined on NIH3T3 cells as previously described using dilutions of virus. In the presence of polybrene a titer of $1 \times 10^7$ I.U./ml was established. To generate virosome complexes a 20 µl aliquot of virus stock was added to 0.5 ml of serum free DMEM plus the appropriate amount of amphiphile and incubated for 30 minutes at room temperature to allow complex formation to occur. For titer estimation each respective complex was prepared in 3 ml with 10% serum containing medium then added to NIH3T3 cells and left for 24 hours for infection to occur.

Example 1

Induction of Liver Cell Proliferation—Dose Respose Curves for Individual Factors Dose response curves were initially performed to identify the dose at which KGF and T3 independently cause maximum hepatocyte proliferation at 24 hours. KGF at 1 mg/kg injected subcutaneously was found to produce maximal proliferation. T3 at 4 mg/kg injected subcutaneously was found to produce maximal proliferation.

Example 2

Induction of Liver Cell Proliferation—Time Course for Individual Factors

Figure 2:
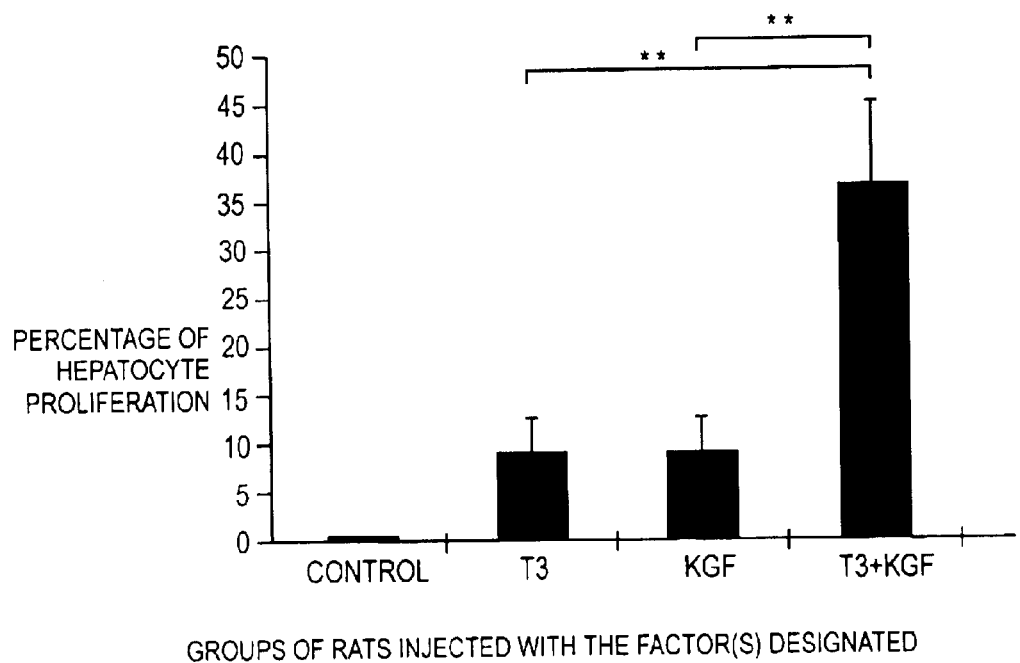
FIG. 2 is a bar graph representing in vivo hepatocyte proliferation at 24 hours following a single and combined growth factor stimulation. Groups of four rats were administered either a single growth factor or a combination of two growth factors. A group of three rats received injections of the growth factor diluents only. T3 (4 mg/kg) and KGF (1 mg/kg) were administered at 0 hours. All animals received BrdU at 23 hours and were killed at 24 hours. Hepatic BrdU incorporation was analyzed as described in detail in the examples infra. Hepatic BrdU incorporation was detected in 4 μm sections by a monoclonal antibody. Results represent mean±S.D. "**" indicate a $p<0.05$.

The times after injection having maximum liver cell proliferation (as measured by DNA synthesis), were also independently established for each of the individual factors. An injection corresponding to the dose producing maximal cell proliferation, as established in Example 1, was independently administered to 2 groups of subjects, one group for each factor. Dividing cells were labelled by administering BrdU 1 hour prior to sacrifice. At 6, 9, 12, 15, 18, 24, and 30 hours after injection three animals of each group were sacrificed and labelled liver cells counted. As shown in FIG. 1, 1 mg/kg KGF injected subcutaneously was found to produce maximal cell proliferation, corresponding to approximately 9%, 24 hours after injection. As shown in FIG. 2, 4 mg/kg T3 injected subcutaneously was found to produce maximal cell proliferation, corresponding to approximately 10%, 24 hours after injection. KGF was found to produce cell proliferation in all zones of the liver. T3 was found to produce cell proliferation predominantly in the mid-zonal region.

Example 3

Unexpected Liver Cell Proliferation Effects Found to Result from Administration of Combination While searching for a manner of producing a clinically acceptable level of liver cell proliferation without a need for prior injury to the liver, a series of experiments were performed whereby a combination of factors was administered to subjects and liver cell proliferation measured 24 hours after administration. Three factor combinations were independently tested, each combination in a different group of animals. A first group received 4 mg/kg T3 at 0 hours. A second group received 1 mg/kg KGF at 0 hours. A third group received 1 mg/kg KGF and 4 mg/kg T3 at 0 hours. A fourth group served as control and received the vehicle or diluent only.

The results of the experiment are shown in FIG. 2. Following a single injection of T3, approximately 10% of hepatocytes are induced into S-phase at 24 hours. Similarly, following KGF injection, approximately 9% of hepatocytes are proliferating at 24 hours. The combination of T3 and KGF results in approximately 35% proliferating hepatocytes at 24 hours.

These in vivo tests showed significantly improved liver cell proliferation when a combination of T3 and KGF are administered, when compared to liver cell proliferation levels resulting from the administration of individual factors. In particular, the increased proportion of liver cells proliferating when a combination of T3 and KGF is administered has been found to be much greater than would have been predicted given the known in vivo proliferative response of liver cells to the individual growth factors. Administration of a combination of factors yielded a semi-synchronous wave of liver cell proliferation involving a significantly larger extent of liver cells compared to the administration of a similar amount of individual factors when administered independently. These improvements are surprising and valuable, for they provide in vivo liver cell proliferation in a range that is clinically useful and substantially equivalent to that obtained by partial hepatectomy, but without a need to cause prior injury to the liver.

Example 4

Cumulative Hepatic Proliferation

Figure 3:
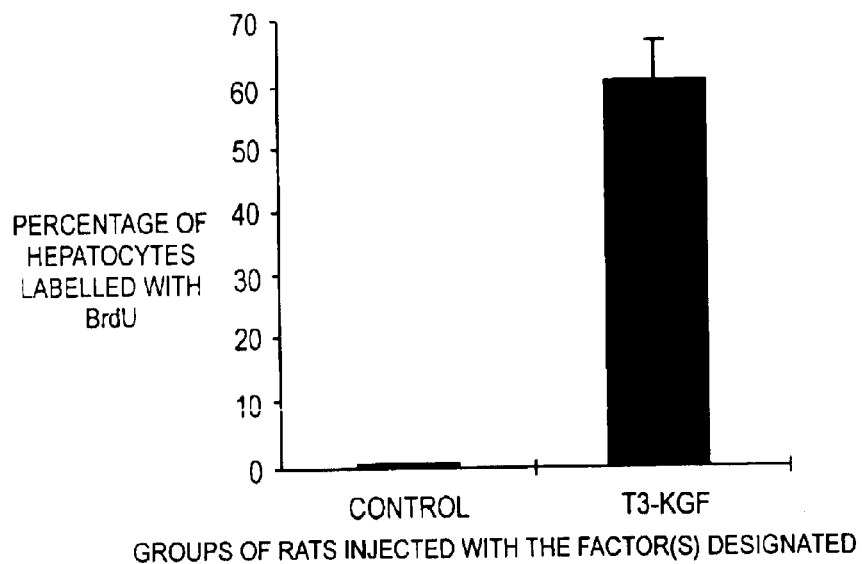
FIG. 3 is a bar graph representing the cumulative proliferation measured following growth factor stimulation. T3 (4 mg/kg) together with KGF (1 mg/kg) were injected subcutaneously into a group of 3 rats. Two rats were injected with vehicle only. BrdU was injected at five hourly intervals between 12 and 32 hours in order to label all hepatocytes entering S-phase. Animals were killed at 33 hours and analysis of BrdU was made as described in detail in the examples infra. Result represent mean±S.D. "**" indicate a $p<0.05$.

Cumulative hepatic proliferation resulting from co-administration of T3 and KGF was determined as follows. At 0 hours, 4 mg/kg T3 and 1 mg/kg KGF were administered by subcutaneous injection into a group of 3 rats. A control group of 2 animals received injections of the diluents only. Animals were labelled every 5 hours with BrdU between hours 12 and 32. The animals were sacrificed at 33 hours and incorporation of BrdU in liver cells was measured. The results of the experiment are shown in FIG. 3. Animals administered T3 and KGF had approximately 60% of their liver cells labelled with BrdU. Notably, significant biliary cell proliferation was also observed.

Example 5

Figure 4:
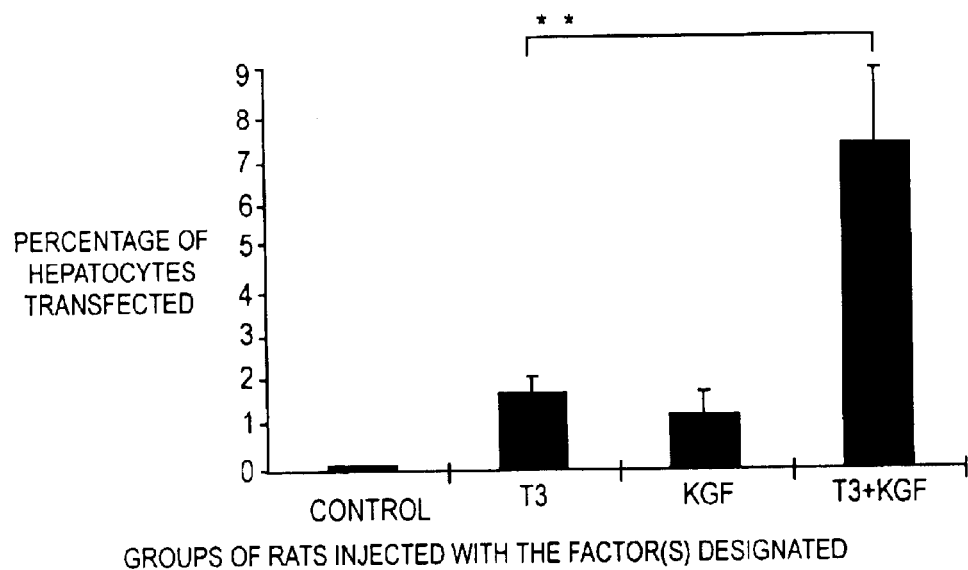
FIG. 4 is a bar graph representing the proportion of hepatocytes expressing β-galactosidase at 9 days following intraportal injection of the TELCeB/AF-7 retrovirus. Groups of four rats received injections of either a single or a combination of growth factors. A group of three control rats received injections of the growth factor diluents only. At 24 hours all rats were injected intraportally with 1 ml of retrovirus during temporary hepatic artery and portal vein occlusion. All rats were sacrificed 9 days after vector administration. The proportion of hepatocytes expressing β-galactosidase was counted from 2000 hepatocytes in three different areas, as described in detail in the examples infra. Results represent mean±S.D. "**" indicate a $p<0.05$.

Induction of Liver Cell Proliferation in vivo by Administration of Combination of Factors Results in Enhanced Transduction of Liver Cells by Retroviral Vectors Having found an effective method of inducing liver cell proliferation within the intact liver, it was next investigated whether a rise in in vivo retroviral transduction corresponding to the increased proliferation of liver cells would result. At hour 0, several groups of four rats received an administration of either a single growth factor (either 4 mg/kg T3 or 1 mg/kg KGF) or the combination of 4 mg/kg T3/1 mg/kg KGF. A control group of three rats received injections of the growth factor diluents only. At 24 hours all rats were injected intraportally with 1 ml of retrovirus during temporary hepatic artery and portal vein occlusion. All rats were killed 9 days following vector administration. As seen in FIG. 4, increased cellular proliferation when a combination of factors is administered gives rise to an unexpectedly greater than corresponding rise in the in vivo retroviral transfection efficiency. It was found that if the liver was primed by a single growth factor prior to intraportal vector administration then between $1.2 \pm 0.4\%$ and $2.3 \pm 0.5\%$ of hepatocytes were transfected. Following T3 administration the transfected hepatocytes were mostly found in the midzonal region. Following KGF administration the transfected hepatocytes were found in all zones of the liver. Following the combined administration of T3 and KGF, the proportion of hepatocytes transfected rose to approximately 7% and these were found throughout all zones of the liver.

The proportion of liver cells transduced following administration of a combination of T3 and KGF was significantly higher than expected, even after taking into account the greater proportion of proliferating cells. While a single injection of T3 induces approximately 10% of liver cells into S-phase at 24 hours, with approximately 1.2% of liver cells being transduced (a ratio of 8.3:1 infectivity), and while after a KGF injection, approximately 9% of hepatocytes are proliferating at 24 hours, with approximately 1% of liver cells being transduced (a ratio of 9:1 infectivity), the combination of T3 and KGF results in approximately 35% proliferating liver cells at 24 hours, with approximately 7% of liver cells being transduced, a superior and unexpected infectivity ratio 5:1.

Example 6

We have also found that the retroviral construct can be administered by the more clinically acceptable peripheral vein intravenous route during liver hyperplasia and still effectively transfect the liver, and that the efficiency of transfection is increased with multiple administrations of the vector.

Figure 5:
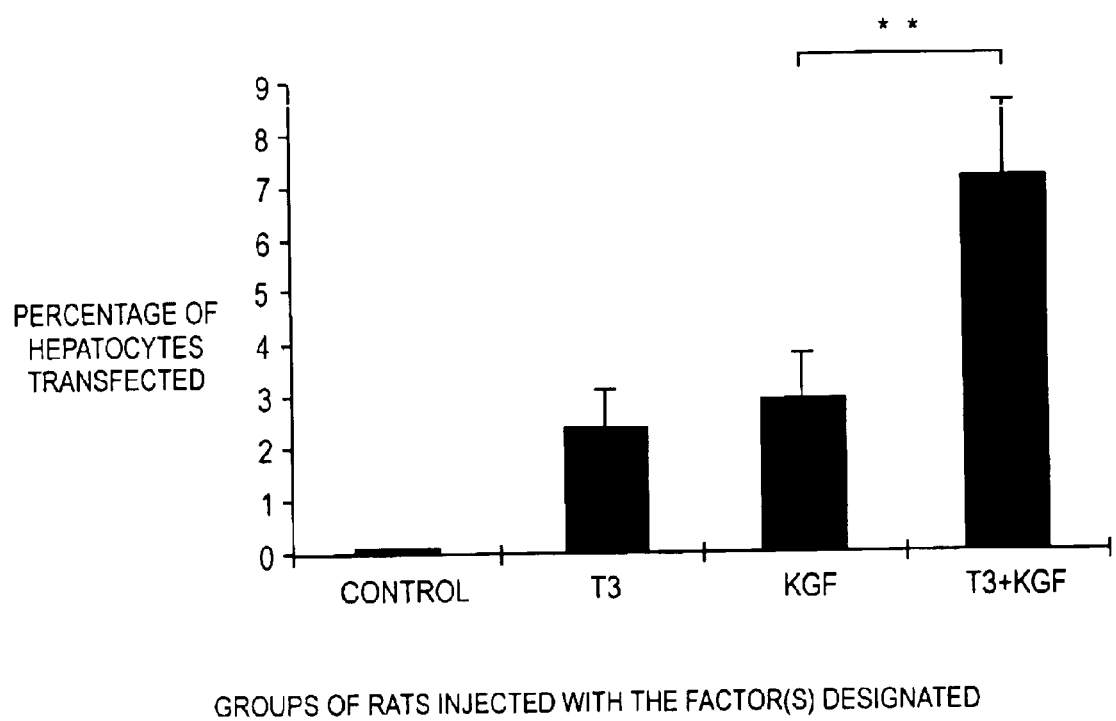
FIG. 5 is a bar graph representing the number of cells transduced following growth factor induced hyperplasia and peripheral venous administration of the retroviral vector. Three groups of 4 rats received an injection of either T3 or KGF, or both growth factors. Two rats were injected with diluent only. All rats received 3 tail vein injections of 1 ml of the TELCeB/AF-7 vector at 18, 24 and 30 hours and were killed at day 10. All animals were sacrificed at day 10 and hepatic β-galactosidase expression was quantified as described in detail in the examples infra. Results represent mean±S.D. "**" indicate a $p<0.05$.

The effects of multiple administrations of retroviral vector and the efficacy of using the more clinically acceptable peripheral vein intravenous administration for the retroviral vector were tested. Several groups of 4 animals received either T3 (4 mg/kg), KGF (1 mg/kg), or T3/KGF at 0 hours. Two control animals were injected with growth factor diluent only. All animals received 3 tail vein injections of 1 ml of the TELCeB/AF-7 vector at 18, 24 and 30 hours and were killed on day 10. Hepatic expression of nuclear localized β-galactosidase was quantified. The animals that had received the combination growth factor prior to the vector administration had the most efficient transfection with 6+% of their hepatocytes expressing the transgene throughout all zones of the liver, except the peri-venous area. (FIG. 5).

Thus, combinations and methods for inducing a semi-synchronous wave of liver cell proliferation in vivo are disclosed. Also disclosed are compositions and methods for enhancing in vivo liver cell transduction by liver directed gene transfer vectors. While embodiments and applications of this invention have been shown and described, it will be apparent to those skilled in the art that many modifications are possible without departing from the inventive concepts herein. For example, while the example describes the expression of a marker gene, β-galactosidase, in vivo in the liver of experimental animals, those of skill in the art will recognize that different RNAs, including ribozymes and anti-sense RNAs, polypeptides and proteins may be expressed in the liver of a variety animals. Proteins and polypeptides may be secreted into the gastrointestinal tract by expression in the biliary tract, or into the blood stream by expression in the liver, if the protein or polypeptide have appropriate, well known in the art, leader sequences. As will be recognized by those of skill in the art, different vectors, and in particular different retroviral vectors may be used with the present invention. Those of skill in the art will also recognize that other promoters and enhancers, including constitutive, liver specific, biliary cell specific or hepatocyte specific promoters, enhancers or combinations thereof may be used, including viral promoters and enhancers like those from the several forms of hepatitis virus, and the like, liver specific promoter/enhancers, or promoters/enhancers from liver specific genes. Inducible promoters/enhancers are also well known in the art and may be used. Alternatively promoters/enhancers that are responsive to internal signals, like sex hormones, sugar levels, circadian rhythm signals, and the like may be used. Moreover, expression may be restricted to biliary tract cells, hepatocytes, or both, in particular by use of appropriate promoter/enhancer combinations. Expression may be of any RNAs, proteins or polypeptides, naturally occurring or engineered, including dominant negative effect proteins, which may be accomodated by the is liver-directed gene transfer vector and that is capable of being transcribed, and if necessary translated by liver cells. The gene construct may also include introns, poly-adenilation signals, and the like, known to affect the half-life of RNA, and/or its level of expression, or to permit another level of regulation. The invention, therefore is not to be restricted except in the spirit of the appended claims.

We claim:

1. A method for improving the efficiency of in vivo liver cell retroviral transduction, the method comprising, inducing a semi-synchronous wave of in vivo liver cell proliferation by concurrently administering tri-iodothyronine (T3) and keratinocyte growth factor (KGF), and further comprising administering to the liver a retroviral vector complexed with cationic liposomes subsequent to the induction of liver cell proliferation, thereby increasing transduction efficiency.

2. The method of claim 1, the cationic liposome comprising DiOctadecylamidoGlycylSpermine (DOGS).

3. A method for treating cirrhosis of the liver comprising concurrently administering to a subject an effective amount of T3 and an effective amount of KGF, thereby inducing a semi-synchronous wave of liver cell proliferation in vivo, and further comprising administering to a liver cell a retroviral vector complexed with cationic liposomes wherein the retroviral vector encodes hepatocyte growth factor (HGF), which treats cirrhosis of the liver.

4. The method of claim 3, wherein the effective amount of T3 ranges from about 400 μg per kg of body weight of the subject to about 40 mg per kg of body weight of the subject.

5. The method of claim 4, wherein the effective amount of T3 is about 4 mg per kg of body weight of the subject.

6. The method of claim 3, wherein the effective amount of KGF ranges from about 100 μg per kg of body weight of the subject to about 10 mg per kg of body weight of the subject.

7. The method of claim 6, wherein the effective amount of KGF is about 1 mg per kg of body weight of the subject.

8. The method of claim 3, wherein the effective amount of T3 and the effective amount of KGF is in a weight ratio of about 4:1.

9. The method of claim 8, wherein the effective amount of T3 is in a dose of about 4 mg per kg of body weight of the subject and the effective amount of KGF is in a dose of about 1 mg per kg of body weight of the subject.

10. The method of claim 9, wherein the T3 and KGF is administered subcutaneously.

11. The method of claim 9, wherein the T3 and KGF is administered intravenously.

12. The method of claim 9, wherein the T3 and KGF is administered intramuscularly.

13. The method of claim 9, wherein the T3 and KGF is administered intraperitoneally.

14. The method of claim 9, wherein the T3 and KGF is administered directly into the liver.

15. The method of claim 3, the cationic liposome comprising DiOctadecylamidoGlycylSpermine (DOGS).

16. The method of claim 3, wherein the retroviral vector is administered between about 6 hours and 14 days after administration of the T3 and KGF.

17. The method of claim 3, wherein the retroviral vector is administered between about 24 hours and 8 days after administration of the T3 and KGF.

* * * * *

UNITED STATES PATENT AND TRADEMARK OFFICE
CERTIFICATE OF CORRECTION

PATENT NO.  : 6,790,838 B2
DATED       : September 14, 2004
INVENTOR(S) : Malcolm R. Alison et al.

It is certified that error appears in the above-identified patent and that said Letters Patent is hereby corrected as shown below:

Column 16,
Lines 58, 60, 62, 64 and 66, change "is" to -- are --.

Signed and Sealed this

Twenty-fifth Day of January, 2005

JON W. DUDAS
*Director of the United States Patent and Trademark Office*